United States Patent [19]

Francis et al.

[11] 4,140,002
[45] Feb. 20, 1979

[54] IMPACT SOUND STRESSING HOLDING ASSEMBLY

[75] Inventors: James F. Francis, Poughkeepsie; Eric W. Hearn; Ralph G. Dessauer, both of Wappingers Falls, all of N.Y.

[73] Assignee: The United States of America as represented by the Secretary of the Air Force, Washington, D.C.

[21] Appl. No.: 902,134

[22] Filed: May 2, 1978

[51] Int. Cl.² ............................................. G01N 3/32
[52] U.S. Cl. ............................................. 73/12; 73/7
[58] Field of Search ............................................. 73/12, 7

[56] References Cited

U.S. PATENT DOCUMENTS 4,004,449  1/1977  Gorey et al. ............................ 73/12

Primary Examiner—Anthony V. Ciarlante
Attorney, Agent, or Firm—Joseph E. Rusz; Arsen Tashjian

[57] ABSTRACT

A holding assembly for impact sound stressing semiconductor wafers and the like including a novel fixture for securing the wafer across a sound tube by clamping between Teflon rings. A cover membrane is also secured across the sound tube to create a closed space defined by the sound tube, cover membrane and semiconductor wafer. Tungsten spheres located in the closed space bounce between the wafer and the membrane when vibrations are propagated in the sound tube for impact sound stressing the semiconductor wafer.

4 Claims, 3 Drawing Figures

IMPACT SOUND STRESSING HOLDING ASSEMBLY

STATEMENT OF GOVERNMENT INTEREST

The invention described herein may be manufactured and used by or for the Government for governmental purposes without the payment of any royalty thereon.

BACKGROUND OF THE INVENTION

This invention relates to a holding fixture for impact sound stressing semiconductor materials and, more particularly, the invention is concerned with providing a novel assembly for inserting, clamping and removing the semiconductor material with improved damage distribution as related to reproducible and uniform clamping pressure and membrane mounting. Variations in wafer thickness are compensated for automatically while loss of impact material is minimized.

Heretofore, insertion and removal of the semiconductor wafer into and out of the holding fixture required considerable time and effort to accomplish. Each wafer had to be clamped separately in the fixture and the operator could unload and reload only a single wafer at a time. Many times the damage distribution was not uniform or reproducible because of the uneven clamping pressure and membrane mounting. Compensation for variations of wafer thickness had to be considered when clamping the wafer material prior to impact sound stressing thereof. Also, loss of considerable quantities of impact material would occur during each insertion and removal of the wafer material.

U.S. Pat. Nos. 4,004,449 and 4,018,626 describe the process and use of impact sound stressing.

SUMMARY OF THE INVENTION

The invention is concerned with providing a holding assembly including a capsule insert suitable for clamping a wafer of semiconductor material therein for treatment by impact sound stressing. The wafer is held between two Teflon rings. Teflon is a tetrafluoroethylene resin manufactured by the E. I. DuPont Co. Inc. of Wilmington, Delaware. A membrane of Teflon, silicon or the like is spaced from the wafer and positioned over the upper Teflon ring and held in position by a membrane clamping ring. A cover pressure plate is provided with two holes therein to allow pressure equalization above the membrane during operation. The cover is positioned above and spaced from the membrane. A cap, preferably of aluminum, holds the assembled capsule insert on the open end of the sound tube.

Accordingly, it is an object of the invention to provide a holding assembly for impact sound stressing semiconductor wafers by an impact medium of tungsten spheres located between the wafer and a cover membrane.

Another object of the invention is to provide an impact sound stressing holding fixture wherein the semiconductor wafer is clamped between two Teflon rings held together by three pins with a membrane clamped in spaced relation above it.

Still another object of the invention is to provide an impact sound stressing holding assembly wherein a capsule insert includes a first Teflon ring, a second Teflon ring above and aligned with the second Teflon ring and a cover/pressure plate above and aligned with the membrane clamping ring.

A further object of the invention is to provide a holding fixture for impact sound stressing of semiconductor wafer material wherein the wafer is held between upper and lower aligned Teflon rings and a membrane is positioned in spaced relation above the wafer with an impacting medium located between the wafer and the membrane.

A still further object of the invention is to provide an impact sound stressing holding assembly wherein a wafer of semiconductor material is held in position by reproducible and uniform clamping pressure with automatic compensation for wafer thickness.

Another still further object of the invention is to provide an improved holding fixture for impact sound stressing semiconductor wafers wherein loss of impact material is held to a minimum.

These and other objects, features and advantages will become more apparent after careful consideration of the following description taken in conjunction with the annexed drawings and appended claims.

DESCRIPTION OF A PREFERRED EMBODIMENT

Figure 1:
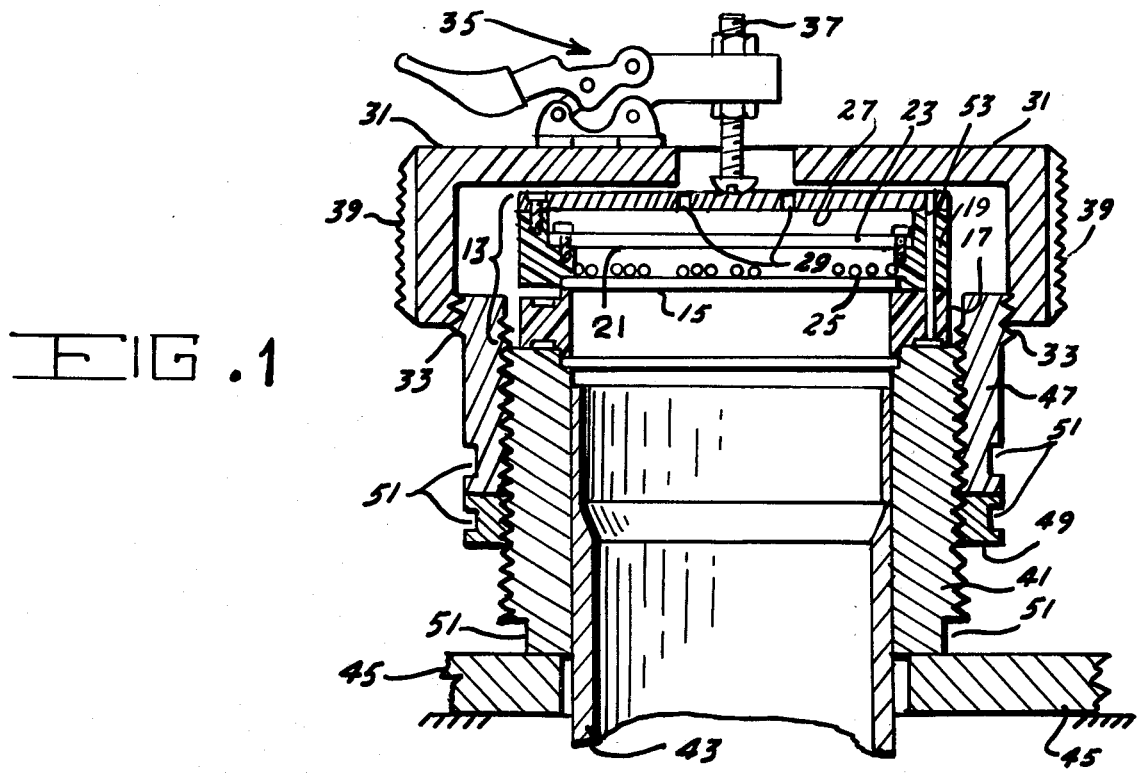
FIG. 1 is a view in cross section of a holding fixture for impact sound stressing semiconductor wafers according to the invention showing the capsule insert which holds the wafer, membrane and impact medium held in position by the clamping arrangement.

Referring now to the Figures wherein like reference characters designate comparable elements in the views, in FIG. 1 there is shown in longitudinal cross section an impact sound stressing holding assembly that includes a capsule insert 13 for holding a wafer 15 of semiconductor material to be processed. The wafer 15 is clamped between a lower Teflon ring 17 and an upper Teflon ring 19. A membrane 21 is clamped above the wafer 15 and spaced therefrom and held in place by a stainless steel ring 23. An impact medium 25 of tungsten spheres, for example, is disposed in the space between the wafer 15 and the cover membrane 21. A cover plate 27 is positioned over the capsule insert 13 and completes the structure thereof. Two holes 29 are placed in the cover plate 27 in order to allow pressure equalization above the membrane 21 during operation.

A cap 31 preferably fabricated of aluminum is threadably attached to the holding assembly by means of coarse threads at the point 33 allowing the cap 31 to be attached by turning ¼ to ½ turn. A clamp 35 having an adjustable contact screw 37 is affixed to the top surface of the cap 31. The head of the contact screw 37 makes contact with the top of the cover plate 27 operating to retain the capsule insert 13 tightly within the holding assembly. The cap 31 is provided with a knurled surface 39 in order to facilitate the turning operation to attach and/or remove the cap 31.

An externally threaded sleeve 41 is attached to the sound tube 43. The lower end of the sleeve 41 rests on the support plate 45. An internally threaded collar 47 is threadably attached to the sleeve 41 for adjustable vertical movement relative thereto. An internally threaded locking ring 49 serves to retain the collar 47 in position after adjustment. A series of flats 51 are machined on the collar 47, ring 49 and sleeve 41 for use with a spanner (not shown).

MODE OF OPERATION

In operation, the clamp 35 is opened and the cap 31 removed by turning ¼ to ½ turn and lifting off. The capsule insert 13, including the wafer 15, the upper and lower Teflon rings 17 and 19, the membrane 21, the ring 23, the impact medium 25 and the cover plate 27, is removed and placed with the cover plate 27 down on a work surface. The lower Teflon ring 17 is pried up and removed. The impacting medium 25 of tungsten spheres or the like, is placed on the membrane 21. The wafer 15 of semiconductor material is placed within the upper Teflon ring 19 with the side to be impacted facing down toward the impacting medium 25. The lower Teflon ring 17 is replaced and pushed down firmly on three alignment pins 53 which protrude upward from the upper Teflon ring 19. Guide grooves in the lower Teflon ring 17 held to locate the pins 53 fall into their respective holes. The capsule is then turned over and replaced on the sleeve 41 on the sound tube 43. The cap 31 is replaced and threaded ¼ to ½ turn until friction between the sleeve 41 and support plate 45 is overcome and the sleeve 41 with the sound tube 43 and speaker (not shown) begins to rotate in the support plate 45.

The desired clamping pressure has been previously set by adjusting the contact screw 37 on the clamp 35. The clamp 35 is then closed and the impact sound stressing cycle is started. The collar 47 onto which the cap 31 threads and its locking ring 49 permits adjustment for capsule inserts of different heights. It can be seen that the above described arrangement provides automatic compensation for wafer thickness variations in order to achieve constant clamping pressure. It also provides repeatable and adjustable clamping pressure independent of the operator.

Figure 2:
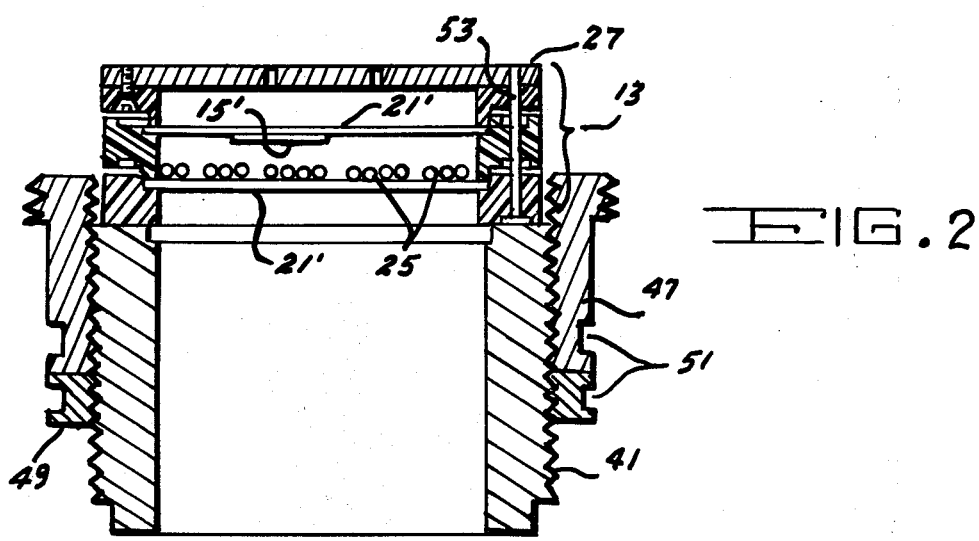
FIG. 2 is a view in cross section of a holding fixture as in FIG. 1 showing an insert arrangement where two spring steel membranes are clamped with the impacting medium therebetween.

In FIG. 2 there is shown a capsule arrangement suitable for impact sound stressing of irregularly shaped samples of semiconductor material. Upper and lower spring steel membranes 21' are clamped with the impacting medium 25 between them. The semiconductor sample 15' is waxed to the underside of the upper membrane 21'. The capsule arrangement shown in FIG. 2 is an accessory for use only in the impact sound stressing of irregularly shaped surfaces. A complete fixture, only for this special purpose, including a superior vacuum alternative to waxing the sample, was published in IBM Technical Disclosure Bulletin, Volume 19, No. 3, August 1976.

Figure 3:
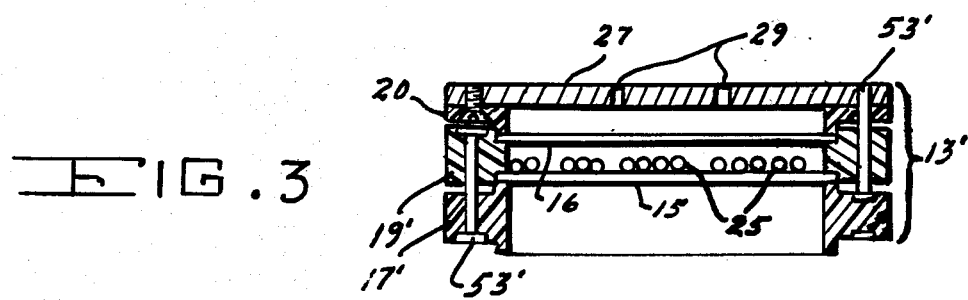
FIG. 3 is a view in cross section of a capsule insert suitable for impact sound stressing two wafers simultaneously and includes an arrangement whereby the impacting medium remains within the capsule while installing and/or removing the wafers.

In FIG. 3 there is shown a capsule insert 13' suitable for the simultaneous impact sound stressing of two wafers 15 and 16 of semiconductor material and provides an arrangement whereby both wafers 15 and 16 can be installed and removed while the impacting medium 25 remains within the capsule 13.

The capsule insert 13 with two wafers 15 and 16 clamped and containing the impacting medium 25 between them is removed from the impact sound stressing assembly (as shown in FIG. 3) and placed on a work surface. The cover plate 27 with the ring 20 attached thereto is pried off the upper Teflon ring 19'. The top wafer 16 is removed and replaced by the next one to be processed. The ring 20 and cover plate 26 are replaced and firmly pushed down; the three pins 53' holding the parts together. The capsule 13 is then turned over with the cover plate 27 on the work surface. The lower Teflon ring 17' is pried off. The lower wafer 15 which has already been impact sound stressed is removed and replaced with the next one to be processed. The lower Teflon ring 17' is replaced and firmly pushed down on the pins 53' on the upper Teflon ring 19'. The capsule 13 is turned over again and is now ready for the next run. The impacting medium 25 of tungsten spheres has remained within the capsule 13 throughout the exchange of the wafers 15 and 16.

Although the invention has been illustrated in the accompanying drawings and described in the foregoing specification in terms of preferred embodiments thereof, the invention is not limited to these embodiments or to the preferred configurations shown. For example, in an alternate model, the stainless steel membrane clamping ring 23 and its screws are replaced by a fluoroelastomer compression gasket which is compressed between the cover plate 26 and the upper Teflon ring 19 holding and sealing the membrane 21. It will be apparent to those skilled in the art that certain changes, modifications and substitutions can be made, particularly with respect to the construction details, without departing from the true spirit and scope of the appended claims.

Having thus set forth the nature of our invention, what we claim and desire to secure by Letters Patent of the United States is:

1. In combination, a holding assembly for impact sound stressing semiconductor material including a sound tube having an open upper end with a capping means for closure thereof and a capsule insert comprising a lower ring of resinous material, an upper ring of resinous material in alignment with said lower ring, a wafer of semiconductor material positioned between said upper and lower rings and held in position thereby, a membrane of material positioned over the top surface of said upper ring and spaced from said wafer, a metallic ring positioned over said membrane for holding said membrane in position and producing an enclosed area between the upper surface of said wafer and the lower surface of said membrane, an impact medium disposed in the enclosed area between said wafer and said membrane, and a cover plate over said membrane and said metallic ring and spaced therefrom, said capsule insert being positioned over the open end of said sound tube under said capping means thereby causing said wafer to be stressed when said impact medium becomes activated by sounds from said sound tube.

2. The combination defined in claim 1 wherein said upper and lower rings of resinous material are fabricated of tetrafluoroethylene resin.

3. The combination defined in claim 2 wherein said cover plate includes openings therein in communication with ambient to allow pressure equalization above the membrane during operation.

4. The combination defined in claim 2 wherein said capping means includes a knurled cap threadably attached to said holding assembly, and clamping means on said cap for maintaining downward pressure on said capsule insert during the impact sound stressing operation.

* * * * *